US009072437B2

(12) United States Patent
Paalasmaa

(10) Patent No.: US 9,072,437 B2
(45) Date of Patent: Jul. 7, 2015

(54) METHOD, APPARATUS AND COMPUTER PROGRAM PRODUCT FOR DETECTING HEART RATE

(75) Inventor: Joonas Paalasmaa, Helsinki (FI)

(73) Assignee: Beddit Oy, Espoo, FL (US)

( * ) Notice: Subject to any disclaimer, the term of this patent is extended or adjusted under 35 U.S.C. 154(b) by 775 days.

(21) Appl. No.: 12/919,736

(22) PCT Filed: Feb. 26, 2009

(86) PCT No.: PCT/FI2009/050165
§ 371 (c)(1),
(2), (4) Date: Oct. 13, 2010

(87) PCT Pub. No.: WO2009/106691
PCT Pub. Date: Sep. 3, 2009

(65) Prior Publication Data
US 2011/0022199 A1 Jan. 27, 2011

(30) Foreign Application Priority Data
Feb. 26, 2008 (FI) .................................... 20085173

(51) Int. Cl.
*G05B 19/42* (2006.01)
*A61B 5/024* (2006.01)
*A61B 5/11* (2006.01)
(Continued)

(52) U.S. Cl.
CPC .............. *A61B 5/024* (2013.01); *A61B 5/1102* (2013.01); *A61B 5/113* (2013.01); *A61B 5/6887* (2013.01); *A61B 5/7267* (2013.01); *A61B 5/7203* (2013.01); *A61B 5/7264* (2013.01); *A61B 7/02* (2013.01); *A61B 5/0205* (2013.01)

(58) Field of Classification Search
CPC ..... A61B 5/024; A61B 5/1102; A61B 5/6887
USPC .................. 700/89; 600/59; 702/190; 706/16
See application file for complete search history.

(56) References Cited

U.S. PATENT DOCUMENTS 5,590,650 A * 1/1997 Genova .......................... 600/301
6,322,514 B1 * 11/2001 Holte ............................. 600/481
(Continued)

FOREIGN PATENT DOCUMENTS

EP 1563286 A2 8/2005
EP 1623667 A1 2/2006
(Continued)

OTHER PUBLICATIONS

Woodward, et al., "Estimating heart rate and RSA from the mattress-recorded kinetocardiogram," Psychophysiology, vol. 44, Jul. 2007, pp. 635-638.
(Continued)

*Primary Examiner* — Sean Shechtman
*Assistant Examiner* — Sivalingam Sivanesan
(74) *Attorney, Agent, or Firm* — Ziegler IP Law Group, LLC

(57) ABSTRACT

A method includes retrieving a signal that measures an activity of a cardiac system. A heart beat model is created based on the retrieved signal, and heart beats are detected using the heart beat model. The model can be trained using a machine learning technique and also respiratory cycle phase information can be used in training the model. A related algorithm, apparatus and computer program are also included.

17 Claims, 5 Drawing Sheets

(51) Int. Cl.
*A61B 5/00* (2006.01)
*A61B 5/113* (2006.01)
*A61B 7/02* (2006.01)
*A61B 5/0205* (2006.01)

(56) References Cited

U.S. PATENT DOCUMENTS

| | | | |
|---|---|---|---|
| 8,046,058 B2* | 10/2011 | Lin et al. | 600/509 |
| 8,346,349 B2* | 1/2013 | Guttag et al. | 600/509 |
| 2002/0045806 A1 | 4/2002 | Baker et al. | |
| 2003/0187337 A1 | 10/2003 | Tarassenko et al. | |
| 2003/0233034 A1* | 12/2003 | Varri et al. | 600/301 |
| 2006/0074823 A1* | 4/2006 | Heumann et al. | 706/16 |
| 2007/0118054 A1* | 5/2007 | Pinhas et al. | 600/587 |
| 2007/0149883 A1* | 6/2007 | Yesha | 600/485 |
| 2009/0043216 A1* | 2/2009 | Lin et al. | 600/501 |
| 2009/0192394 A1* | 7/2009 | Guttag et al. | 600/509 |
| 2011/0257536 A1* | 10/2011 | Ser et al. | 600/484 |
| 2012/0041326 A1* | 2/2012 | Korenweitz | 600/509 |
| 2013/0046193 A1* | 2/2013 | Guttag et al. | 600/509 |

FOREIGN PATENT DOCUMENTS

| | | | | |
|---|---|---|---|---|
| WO | 03/055395 A1 | 7/2003 | | |
| WO | WO 03/055395 A1 * | 7/2003 | | G05F 17/00 |
| WO | 2006/003243 A1 | 1/2006 | | |
| WO | 2007/101343 A1 | 9/2007 | | |
| WO | WO 2007143535 A2 * | 12/2007 | | A61B 5/08 |
| WO | 2009/023524 A1 | 2/2009 | | |

OTHER PUBLICATIONS

Brink, et al., "Contact-free measurement of heart rate, respiration rate, and body movements during sleep," Behavior Research Methods, vol. 38, 2006, pp. 511-521.

Chan, et al., "Heartbeat Detection Using Energy Thresholding and Template Match," Proceedings of the 2005 IEEE Engineering in Medicine and Biology 27th Annual Conference, Shanghai, China, Sep. 1-4, 2005.

Gonzalez, et al., "Period estimation using minimum entropy deconvolution (MED)," Signal Processing, vol. 41, Jan. 1995, pp. 91-100.

Kohler, et al., "The Principles of Software QRS Detection," IEEE Engineering in Medicine and Biology, Jan./Feb. 2002, pp. 42-57.

Lin, et al., "Heart Rate Detection in Highly Noisy Handgrip Electrocardiogram," Computers in Cardiology 2008; vol. 35, pp. 477-480.

Masloboev, et al., "A Monitor of Biomedical Cardiac Activity," Biomedical Engineering, vol. 38, No. 4, 2004, pp. 165-169. Translated from Meditsinskaya Tekhnika, vol. 38, No. 4, 2004, pp. 3-8. Original article submitted Feb. 5, 2004.

Okada, et al., "Proposal for a Method of Nonrestrictive Measurement of Resting Heart Rate in a Lying Position," Journal of Physiological Anthropology, vol. 25, 2006, pp. 299-305.

Pilgram, et al., "Estimating Respiratory Rate from Instantaneous Frequencies of Long Term Heart Rate Tracings," Computers in Cardiology 1993, pp. 859-862.

Suarez, et al., "ECG Beat Detection Using a Geometrical Matching Approach," IEEE Transactions on Biomedical Engineering, vol. 54, No. 4, Apr. 2007, pp. 641-650.

"Supervised Learning", Wikipedia, the free encyclopedia, <http://en.wikipedia.org/wiki/Supervised_learning>, accessed Jan. 23, 2009.

Wei, et al., "Semi-Supervisde Time Series Classification," Department of Computer Science and Engineering, University of California, Riverside.

* cited by examiner

METHOD, APPARATUS AND COMPUTER PROGRAM PRODUCT FOR DETECTING HEART RATE

CROSS-REFERENCE TO RELATED APPLICATIONS

This application is the US National Stage of International Application No. PCT/FI2009/050165, filed on 26 Feb. 2009, which designated the United States of America and which was published under PCT Article 21 (2) as Publication No. WO2009/106691 A1 and which claims priority to and the benefit of Finnish Application No. 20085173, filed 26 Feb. 2008, the disclosures of which are incorporated herein by reference in their entireties.

BACKGROUND

1. Field

The disclosed embodiments relate to methods, apparatus and computer program products for detecting heart rate.

2. Background

There are various methods for contactless measurement of the heart rate of a person lying on a bed. A fair share of the methods are based on measuring the almost periodically repeating vibrations of the heart by analyzing the output signal of a force sensor that measures the horizontal or vertical vibrations of the body. An example of a force sensor has been presented in the European patent publication EP 1 563 286.

In addition to the force sensor, the heart rate analysis system requires a signal processing unit that extracts the heart rate from the sensor's signal using a signal processing algorithm. These algorithms conventionally use strategies such as cross-correlation with the beat prototype, as suggested in S. H. Woodward et al., "*Estimating heart rate and RSA from the mattress-recorded kinetocardiogram*," Psychophysiology, vol. 44, July 2007, pp. 635-638, bandpass filtering, as suggested in international patent application publication WO 2006/003243, or peak detection, as suggested in S. Okada et al., "*Proposal for a Method of Non-restrictive Measurement of Resting Heart Rate in a Lying Position*," Journal of PHYSIOLOGICAL ANTHROPOLOGY, vol. 25, 2006, pp. 299-305.

A drawback of the prior art signal processing algorithms is that typically they are able to detect the heart rate reliably only if the monitored person stays still and does not make any movements that would distort the signal. Movements such as speaking or waving a hand may render the algorithms useless.

SUMMARY

According to a first aspect of the disclosed embodiments there is provided a method, comprising retrieving a signal that measures an activity of a cardiac system, wherein the method further comprises creating a heart beat model based on the retrieved signal; and detecting heart beats using the heart beat model.

In certain embodiments, the activity of the cardiac system means mechanical activity of the cardiac system. Accordingly, the signal that measures an activity of the cardiac system measures mechanical activity of the cardiac system. Examples of signals that are indicative of (or measure) mechanical activity of the cardiac system are a movement signal and an acoustic signal. In certain embodiments, the signal is a ballistocardiography signal.

By a movement signal is typically meant a signal measuring the mechanical movements of a monitored person. A movement signal is generally obtained by measuring for example the displacement, acceleration or velocity of the body or body part. A movement signal may be received for example from a force sensor, an acceleration sensor or a radar system. Movement signals can in some connections also be called as mechanical movement signals or mechanical signals.

By an acoustic signal is typically meant a signal measuring the acoustic activity of the cardiac system. An acoustic signal may be received for example from an electronic stethoscope or a microphone.

Movement signals and acoustic signals can be measured for example from parts of the body, the whole body, a structure supporting the body or a structure supporting a part of the body.

In certain embodiments, the method further comprises updating the heart beat model by training the model using a machine learning technique, such as supervised learning.

In certain embodiments, the method comprises using heart beat shape information and/or heart beat interval information and/or respiratory cycle phase information in training the model.

In certain embodiments, the heart beat model is a supervised learning classifier.

In certain embodiments, the method further comprises providing an estimation of an expected heart beat shape based on the model.

In certain embodiments, the method comprises using information about a respiratory cycle phase in training the heart beat model.

In certain embodiments, the method comprises calculating an estimation of heart beat onset times; and using the estimation in the detection of heart beats.

Yet in certain embodiments, the method comprises creating an inverse model of an original heart beat shape that gives as a result the shape of the heart beat before it has been mixed with adjacent beats; and solving the inverse model and using the recovered heart beat shape in heart beat model creation and heart beat detection.

According to a second aspect of the disclosed embodiments there is provided an apparatus, comprising means configured for retrieving a signal that measures an activity of a cardiac system, wherein the apparatus comprises means configured for creating a heart beat model based on the retrieved signal; and means configured for detecting heart beats using the heart beat model.

In certain embodiments, the apparatus is configured to output data directly or indirectly indicative of an instant heart beat rate.

In certain embodiments, the apparatus is configured to update the heart beat model by training the model using a machine learning technique, such as supervised learning. In certain embodiments, the model is a supervised learning classifier.

In certain embodiments, the apparatus is configured to use information about a respiratory cycle phase in training the heart beat model.

In certain embodiments, the apparatus is configured to cancel the interference of overlapping heart beat impulses by inverse modeling.

According to a third aspect of the disclosed embodiments there is provided a computer readable medium having stored thereon a computer program executable in an apparatus, the computer program comprising program code for implementing an algorithm that controls the apparatus to retrieve a signal that measures an activity of a cardiac system, further controls the apparatus to create a heart beat model based on the retrieved signal, and further controls the apparatus to detect heart beats using the heart beat model.

Embodiments of the present disclosure offer an advanced signal processing algorithm that is able to detect the heart rate of a person even if he or she makes some movements during monitoring. A signal processing algorithm introduced by certain embodiments makes heart beat detection more reliable by utilizing information about the respiratory cycle, canceling the interference of adjacent beats as well as building a model of the heart beat's shape.

Various exemplary embodiments of the present disclosure are illustrated hereinafter in the detailed description of the disclosed embodiments as well as in the dependent claims appended hereto. The embodiments are illustrated with reference to selected aspects of the disclosed embodiments. A person skilled in the art appreciates that any embodiment of the present disclosure may apply to other aspects as well either alone or in combination with other embodiments.

BRIEF DESCRIPTION OF THE DRAWINGS

The aspects of the disclosed embodiments will now be described, by way of example only, with reference to the accompanying drawings, in which.

DETAILED DESCRIPTION

Figure 1:
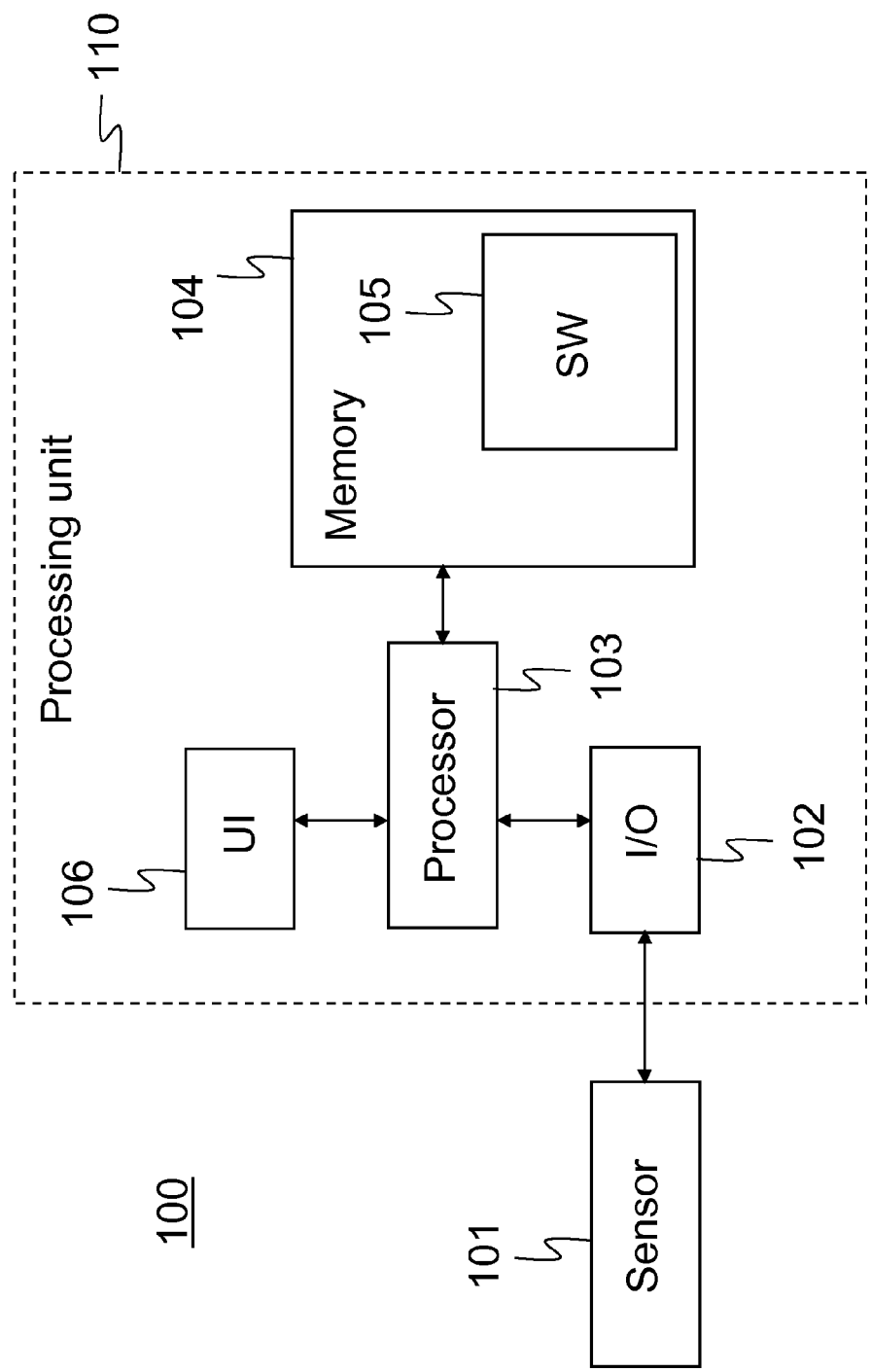
FIG. 1 shows a framework for carrying out selected embodiments of the present disclosure.

FIG. 1 shows an exemplary framework in which selected embodiments of the present disclosure can be implemented. This framework comprises a processing unit 110 which processes a signal containing measurement data on vibrations of a person whose cardiac system is being monitored.

The signal may be retrieved on-line from a sensor 101. The sensor 101 may be a force sensor described in EP 1 563 286 placed in the near proximity of the monitored person (e.g., under a bed post or mattress). The signal is received by the processing unit 110 via a wired or wireless communications method. A suitable communication interface 102, depending on the implementation, is implemented in the processing unit 110. For example, a serial bus or a Bluetooth connection can be used. In a further embodiment, the processing unit 110 can be integrated into the sensor unit 101.

The received signal is processed by a processor 103 of the processing unit 110 in accordance with an algorithm, also referred to as a signal processing algorithm. A memory 104 comprised by the processing unit 110 comprises software 105 containing instructions and/or program code for implementing the algorithm. The signal processing algorithm, when performed, produces desired output, e.g., the heart beat rate and/or heart beat onset times of the monitored person.

Alternatively, instead of using on-line data, the processing unit 110 may process a beforehand stored signal retrieved from the internal memory 104 or from an external memory (not shown).

The processing unit 110 may further contain a user interface controller 106 for receiving user input, e.g., from a keyboard (not shown), and for giving visual output for a user, e.g., in a display unit (not shown).

Figure 2:
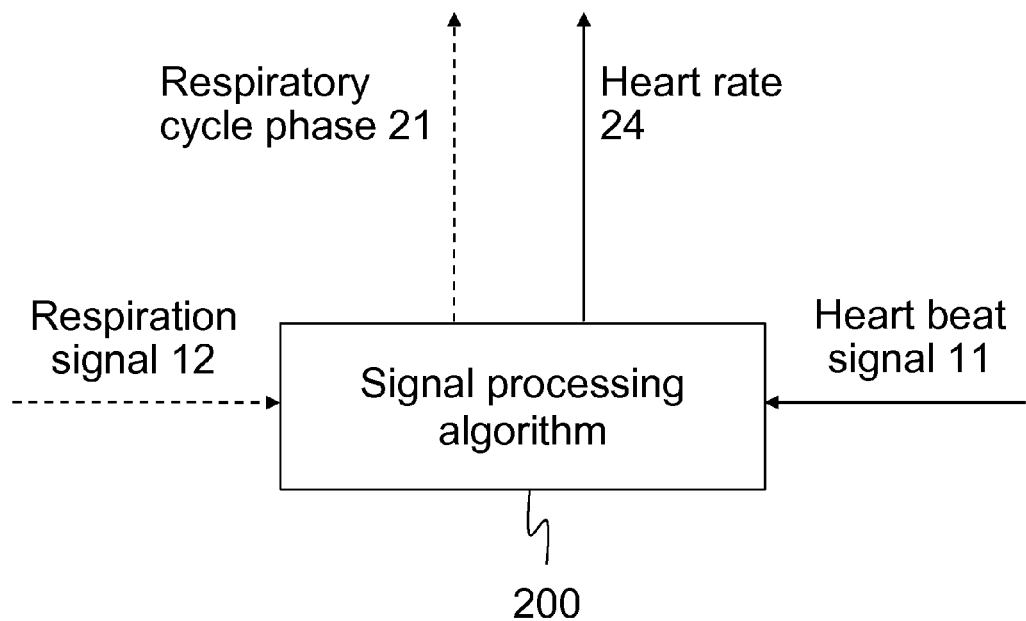
FIG. 2 shows a schematic high-level illustration of an algorithm in accordance with certain embodiments.

FIG. 2 shows a schematic high-level illustration of a signal processing algorithm 200 in accordance with certain embodiments. The algorithm uses at least one input and produces at least one output. In an embodiment, the algorithm 200 uses as an input signal the signal retrieved from the sensor 101 (FIG. 1) or a signal retrieved from a memory, or a corresponding signal. This signal comprises detected vibrations of a monitored body, in particular also vibrations which are due to heart beats. Accordingly, this input signal is here referred to as heart beat signal 11. In a more general embodiment, the heart beat signal 11 is any signal which can be assumed to represent, at least partially, an activity of cardiac system. The signal processing algorithm 200 produces desired output, e.g., the heart beat rate 24. The form of the output may vary depending on the implementation. The output may directly indicate the instant heart rate or indicate the heart rate indirectly, e.g., by outputting its inverse value (reciprocal) or similar.

The signal processing algorithm 200 may optionally use also other inputs, such as a signal which is here referred to as respiration signal 12. In an embodiment, this signal 12 may be the same signal as the heart beat signal 11, as the signal retrieved, e.g., from a sensor also comprises vibrations caused by respiration. In a more general embodiment, the respiration signal 12 is any signal which can be assumed to represent, at least partially, a respiration activity. An optional output of the signal processing algorithm 200 is respiratory cycle phase information 21 indicating a detected phase in a respiratory cycle.

Figure 3:
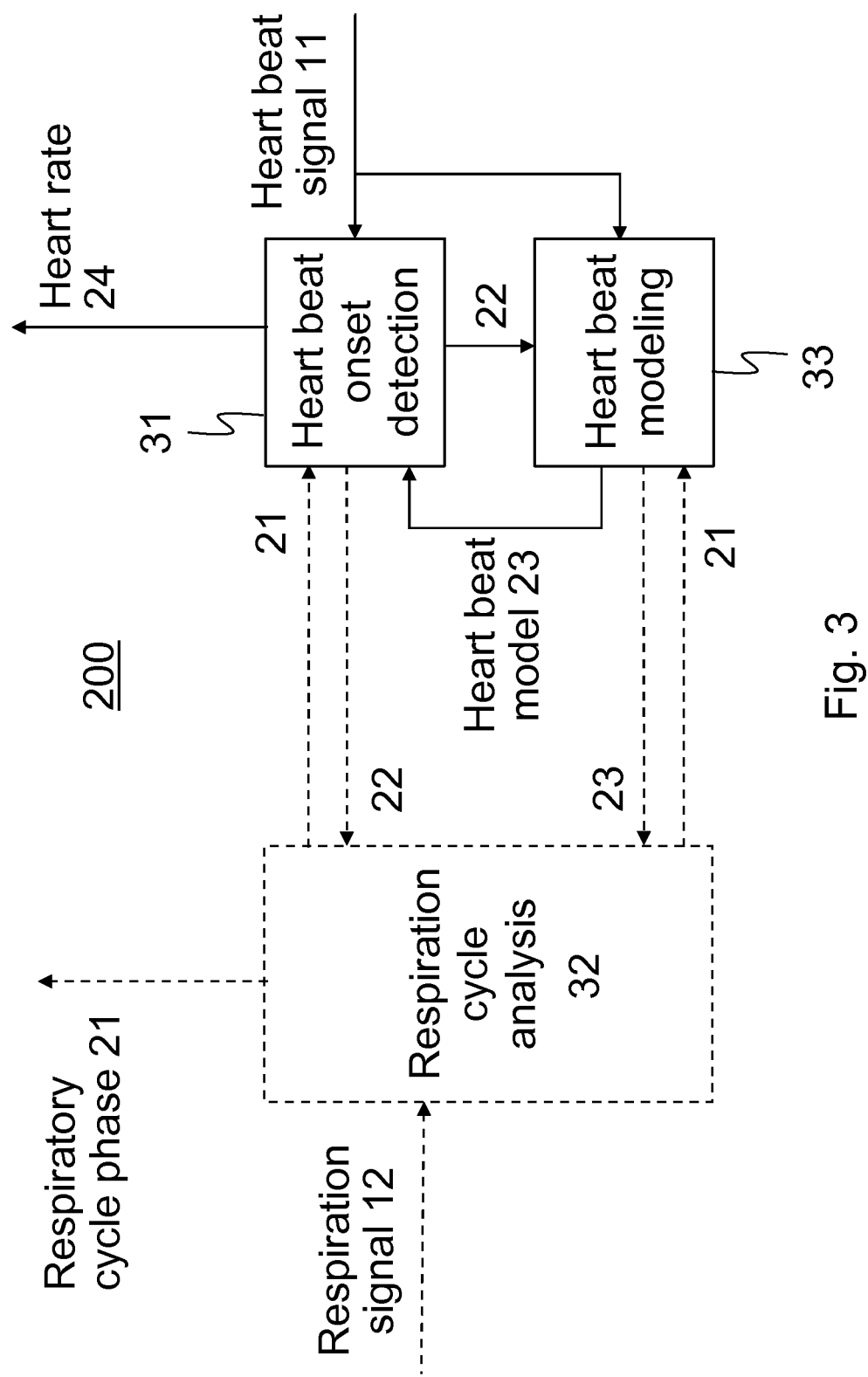
FIG. 3 shows a more detailed illustration of an algorithm in accordance with certain embodiments.

FIG. 3 shows a more detailed illustration of a signal processing algorithm 200 in accordance with certain embodiments.

In an embodiment, the algorithm 200 is divided into three modules: Heart beat onsets are detected in module 31, an optional respiratory cycle analysis is carried out in module 32, and module 33 initializes and maintains a model of the shape of a single heart beat impulse.

Module 31 receives as input the heart beat signal 11, optionally respiratory cycle phase information 21 and the heart beat model 23. Module 31 calculates heart beat onset times 22 from the inputs and outputs them to module 33. Module 31 may also calculate the heart rate 24 based on the heart beat onset times.

The optional module 32 receives as input a signal 12 that can be used to detect the respiratory cycles of the person. Module 32 detects the respiratory cycles from the signal and outputs the respiratory cycle phase information 21 to modules 31 and 33. Module 32 can alternatively also receive inputs 22 and 23 from modules 21 and 23, respectively, with the purpose of enhancing the detection of the respiratory cycle.

Module 33 receives as input the heart beat signal 11, optionally respiratory cycle phase information 21 and heart beat onset times 22. Module 33 creates and maintains the heart beat model 23 based on the inputs and outputs the model 23 to module 31.

In the following the operation of certain embodiments of the present disclosure is explained in yet further detail. As indicated in the preceding, the heart rate of a person can be detected (or calculated) by using a signal processing algorithm which receives as input a signal measuring the cardiac activity of the person.

In its simple form, the procedure followed by the algorithm can basically comprise only the following:
1) Retrieving a signal that measures the activity of the cardiac system;

2) Creating, based on said signal, a model of a heart beat impulse;
3) Detecting heart beats by using the heart beat model.

In certain embodiments, the heart beat model is a supervised learning classifier with one or more input features and one output label. One of the input features is the heart beat shape. The output label is binary and defines if the input variable(s) represent a heart beat (BEAT) or not (NON-BEAT). The heart beat shape input feature of the model can be in the form of a signal segment that represents the shape of a single heart beat impulse or in a transformed form such as a set of wavelet coefficients. The classifier can use any suitable classification method such as naïve Bayes or support vector machines.

The model initialization (creation) phase basically requires only the heart beat signal 11. Initialization is carried out in an embodiment by finding an almost periodically repeating phenomenon from the signal that is repeated at a rate that would be possible for a heart beat (e.g., interval in the range 0.3-2 seconds). If such an almost periodically repeating phenomenon is found, they are likely to be the heart beat impulses in the signal. The heart beat model can be initialized by training it with input-output pairs where each output label is BEAT and the inputs are formed from the positions where beat impulses were found. Also, the model is trained with sufficiently many input-output pairs where each output label is NON-BEAT and the inputs are formed from positions where beat impulses were not found. In an embodiment, the almost periodic phenomenon is found by applying a minimum-entropy deconvolution method to the signal that represents the cardiac activity. The idea of minimum entropy deconvolution is to find a convolution kernel h(n) that, when convolved with the input signal y(n), produces an output signal w(n) with as low an entropy as possible. Entropy can be minimized by maximizing the kurtosis of the output signal w(n). If the input signal contains a repeating phenomenon, they can be located by finding the peaks of w(n). The details of the minimum-entropy deconvolution method as such are known to a skilled person and will not be described here more closely. Alternatively, an autocorrelation method, also known as such, can be applied to the signal instead of the minimum-entropy deconvolution method.

Once module 33 has initialized the heart beat model 23 and starts feeding it to module 31, module 31 starts to detect beat onsets from the heart beat signal 11 with the model.

Detecting the beat onsets from the signal using the model can be done in many ways.

In an embodiment, the signal is windowed to extract the shape of the signal at consecutive time instants. The shapes are fed to the model that classifies them with labels BEAT or NON-BEAT. Window positions that are classified as BEAT are used in an embodiment as beat onset positions 22 and fed to module 33.

When module 33 receives a heart beat onset time 22 from module 31, it extracts in an embodiment the heart beat impulse shape from the heart beat signal 11 using the onset time. Using the extracted heart beat impulse shape, module 33 trains the heart beat model with an input-output pair comprising the heart beat impulse shape and a BEAT label. In addition to training with found beats, shapes that represent segments where a beat cannot be found are used to train the model with the NON-BEAT label.

Figure 4:
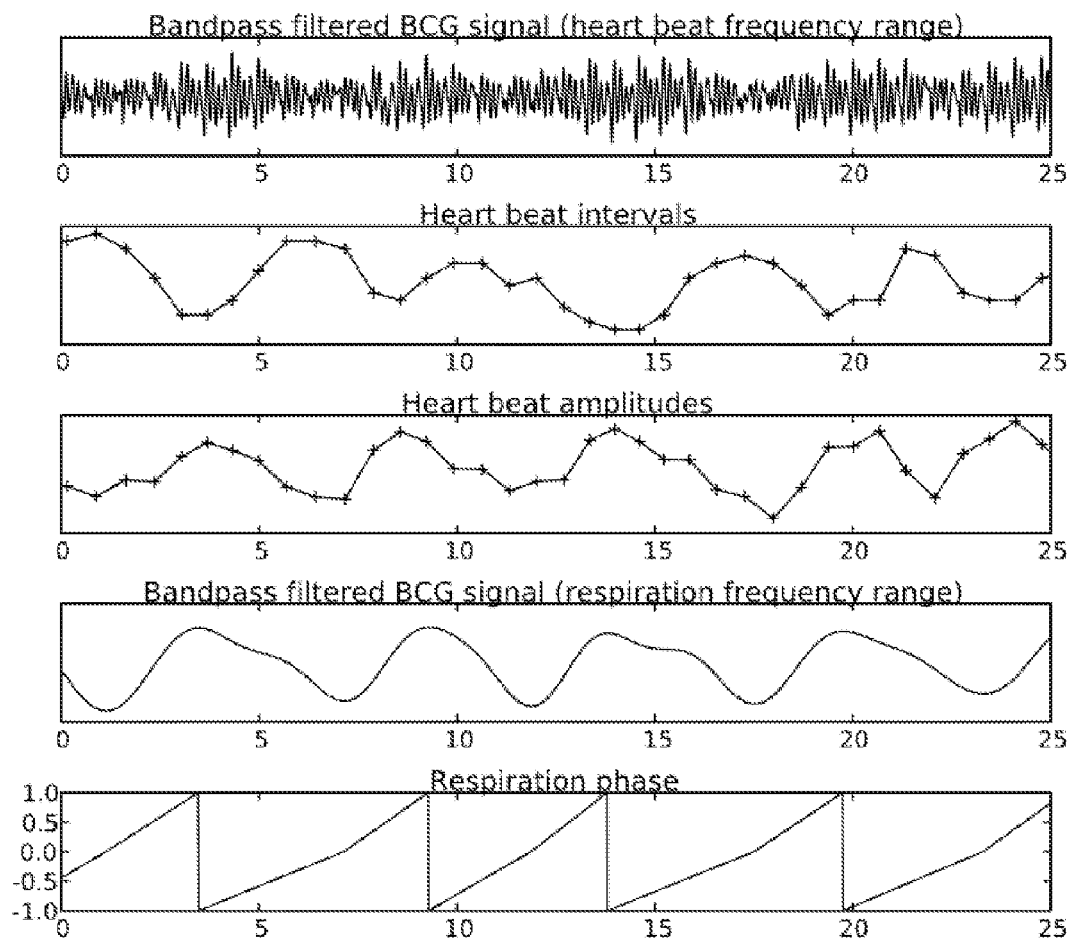
FIG. 4 shows the correlation between heart beat amplitude, interval and respiratory cycle phase in certain embodiments.

In another implementation, the interval to the previous beat onset is used as the model's input feature, in addition to the heart beat shape. In yet another implementation, respiratory cycle phase is used as the model's input feature, in addition to the heart beat shape, with or without using the interval to the previous beat onset as an input feature. If the respiratory cycle phase and/or beat interval are used as input features, they are used in module 33 to train the model and in module 31 to classify signal positions as BEAT or NON-BEAT. The benefit from using these additional input features is that there is a clear correlation between the respiratory cycle phase, heart beat shape and heart beat interval, as illustrated in FIG. 4. The uppermost graph of FIG. 4 shows a high-pass-filtered (with cutoff at 1 Hz) ballistocardiography (BCG) signal. The vertical axis denotes force and the horizontal axis denotes time. The second graph shows heart beat intervals and the third graph heart beat amplitudes during the same observation period. The fourth graph shows the BCG signal after band-pass-filtering (with 0.1-1.0 Hz passband). The lowermost graph shows transitions between the respiratory cycle phases.

It is possible the detect the respiratory cycle from a force sensor signal (or respiration signal) 12 using prior art methods. In accordance with an embodiment, the respiratory cycle is detected, for example, by bandpass-filtering the respiration signal 12 (e.g., with 0.1-1.0 Hz passband) and observing crossings of a pre-defined threshold in the filtered signal. If heart beat information is available, detection can be further aided by utilizing the correlation of heart beat intervals and amplitude with the phase of the respiratory cycle. Accordingly, in order to enhance the respiratory cycle analysis, heart beat interval 22 and/or shape data 23 from the heart beat analysis modules 31 and 33, respectively, can be inputted to the respiratory cycle analysis module 32.

The respiratory cycle is generally modeled mathematically as a cyclic transition between the following states: inhalation begin, inhalation end, exhalation begin, exhalation end. For the purposes of supervised learning, inhalation begin is represented by value −1, inhalation end by 0, exhalation begin by 0, and exhalation end by 1. Transition between the states is illustrated in the lowermost graph of FIG. 4. The horizontal axis denotes time.

Figure 5:
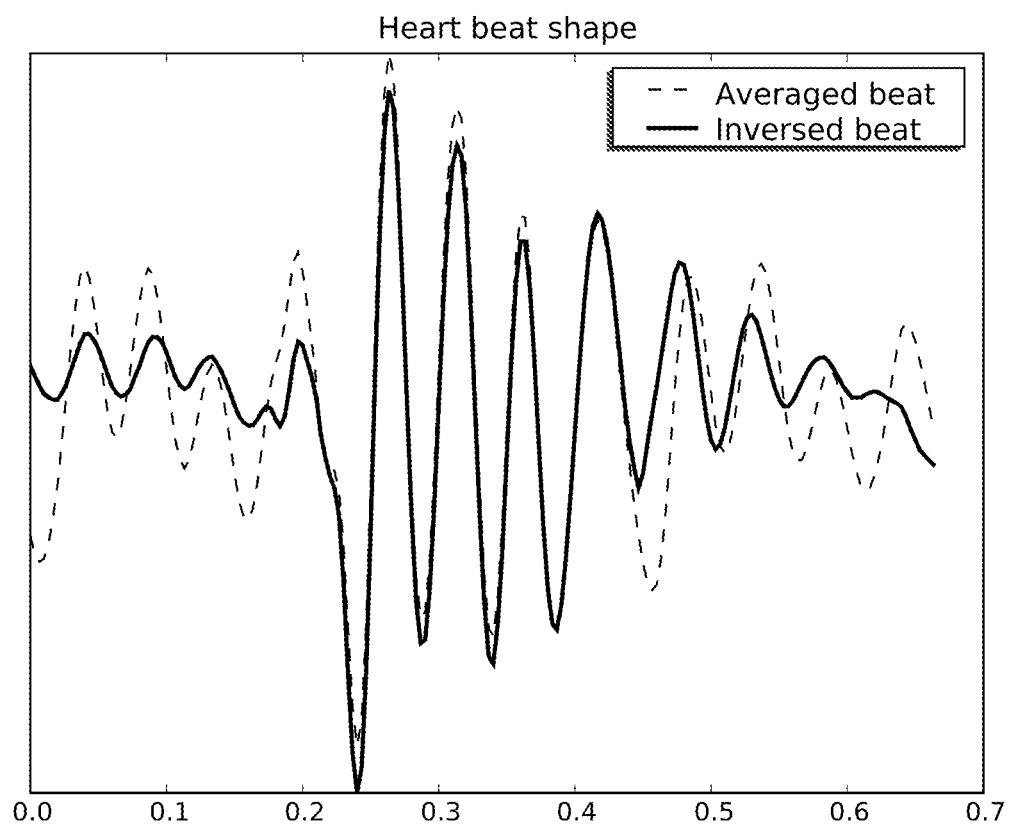
FIG. 5 shows the difference between heart beat shapes extracted using inverse modeling and averaging.

Yet another embodiment concerns canceling the interference of overlapping heart beat impulses. Once module 31 has detected consecutive heart beat onsets, it becomes possible to analyze the shape of the original heart beat impulse prior to its mixing with adjacent heart beats. As a single heart beat impulse generally lasts longer than the interval between heart beats (the interval meaning the reciprocal of the heart rate), the adjacent impulses get mixed making detecting heart beats more difficult. The original impulses can be recovered in an embodiment from the signal by formulating an inverse model that solves the shape of the original beat impulses before they were mixed with adjacent beats. In a simple form, the mixing of beats can be represented with the equation $$y(n) = \sum_{i=1}^{N} s(n - d_i)$$

where s(n) represents a single heart beat impulse, $d_i$ are the N positions of the heart beat impulses and y(n) is the signal after the mixing of the beats. As y(n) (the heart beat signal) and $d_i$, (the heart beat times) are known, s(n) can be solved by formulating the inverse model as a system of linear equations. The result of modeling the heart beat shape is illustrated in FIG. 5. As seen in the figure, the heart beat shape calculated using an inverse model is less distorted by adjacent beats than the shape calculated by just averaging heart beat shapes. The above mentioned inverse model assumes that the heart beat shape is invariant across all heart beats, but the model can be made even more precise by allowing varying shapes for different heart beats.

Canceling the overlapping impulses benefits both modules 31 and 33. In module 33, the heart beat model 23 can be created without interference from adjacent beats, so it becomes more precise. When canceling of overlapping impulses is utilized it module 31, the interference of adjacent beats in the detection of beat onsets is removed so beat detection becomes more precise.

Various embodiments have been presented. It should be appreciated that in this document, words comprise, include and contain are each used as open-ended expressions with no intended exclusivity.

The foregoing description has provided by way of non-limiting examples of particular implementations and embodiments of the present disclosure a full and informative description of the best mode presently contemplated by the inventors for carrying out the aspects of the disclosed embodiments. It is however clear to a person skilled in the art that the disclosed embodiments are not restricted to details of the embodiments presented above, but that it can be implemented in other embodiments using equivalent means without deviating from the characteristics of the present disclosure.

Furthermore, some of the features of the above-disclosed embodiments of this present disclosure may be used to advantage without the corresponding use of other features. As such, the foregoing description should be considered as merely illustrative of the principles of the present disclosure, and not in limitation thereof. Hence, the scope of the disclosed embodiments is only restricted by the appended patent claims.

What is claimed is:

1. A method, comprising:
    retrieving a signal comprising overlapping adjacent heart beat impulses mixed with each other;
    creating a heart beat model of the shape of an original non-mixed single heart beat impulse by applying a representation of the retrieved signal as a summation of original non-mixed single heart beat impulses at known positions; and
    using the created heart beat model to detect heart beats.

2. The method of claim 1, wherein the mixing of heart beat impulses in the retrieved signal in said heart beat model creation is described as a system of linear equations.

3. The method of claim 2, comprising:
    finding the shape of an original non-mixed single heart beat impulse by solving said system of linear equations.

4. The method of claim 1, wherein the signal measures mechanical activity of a cardiac system.

5. The method of claim 1, further comprising utilizing information about a respiratory cycle to detect heart beats.

6. The method of claim 1, wherein the signal is a ballistocardiography signal.

7. The method of claim 1, wherein the signal is a signal from a force sensor.

8. The method of claim 1, comprising outputting data directly or indirectly indicative of a heart beat rate.

9. An apparatus, comprising:
    a processing unit configured to retrieve a signal comprising overlapping adjacent heart beat impulses mixed with each other, the processing unit being further configured to:
    create a heart beat model of the shape of an original non-mixed single heart beat impulse by applying a representation of the retrieved signal as a summation of original non-mixed single heart beat impulses at known positions; and
    the processing unit being further configured to detect heart beats using the created heart beat model.

10. The apparatus of claim 9, wherein the processing unit is configured to describe the mixing of heart beat impulses in the retrieved signal in said heart beat model creation as a system of linear equations.

11. The apparatus of claim 10, wherein the apparatus is configured to find the shape of an original non-mixed single heart beat impulse by solving said system of linear equations.

12. The apparatus of claim 9, wherein the apparatus is configured to output data directly or indirectly indicative of a heart beat rate.

13. The apparatus of claim 9, wherein the apparatus is configured to utilize information about a respiratory cycle to detect heart beats.

14. The apparatus of claim 9, wherein the signal measures mechanical activity of a cardiac system.

15. The apparatus of claim 9, wherein the signal is a ballistocardiography signal.

16. A non-transitory computer readable medium having stored thereon a computer program executable in an apparatus, the computer program comprising:
    program code for implementing an algorithm that controls the apparatus to retrieve a signal comprising overlapping adjacent heart beat impulses mixed with each other, further controls the apparatus to create a heart beat model of the shape of an original non-mixed single heart beat impulse by applying a representation of the retrieved signal as a summation of original non-mixed single heart beat impulses at known positions, and further controls the apparatus to detect heart beats using the created heart beat model.

17. A non-transitory computer readable medium having stored thereon a computer program executable in an apparatus, and when executed configured to implement the method of claim 1.

* * * * *